United States Patent

Schuster et al.

[11] Patent Number: 5,233,078
[45] Date of Patent: Aug. 3, 1993

[54] PREPARATION OF DIALKYL MALONATES

[75] Inventors: Ludwig Schuster, Limburgerhof; Klaus Halbritter, Heidelberg, both of Fed. Rep. of Germany

[73] Assignee: BASF Aktiengesellschaft, Ludwigshafen, Fed. Rep. of Germany

[21] Appl. No.: 894,125

[22] Filed: Jun. 4, 1992

[30] Foreign Application Priority Data

Jun. 22, 1991 [DE] Fed. Rep. of Germany ....... 4120721

[51] Int. Cl.$^5$ .............................................. C07C 67/00
[52] U.S. Cl. .................................... 560/204; 560/190; 560/265; 568/568; 568/590
[58] Field of Search ....................... 560/190, 204, 265; 568/590, 568

[56] References Cited

U.S. PATENT DOCUMENTS 4,251,447  2/1981  Perrin ............................ 546/268 X
4,360,691  11/1982  Perrin ................................ 560/131

Primary Examiner—Jose G. Dees
Assistant Examiner—Vera C. Clarke
Attorney, Agent, or Firm—Keil & Weinkauf

[57] ABSTRACT

The invention relates to a process for preparing dialkyl malonates by ozonolysis of diketene, subsequent catalytic hydrogenation and esterification of the reaction products, the by-products being alkyl formates and dialkyl acetals.

7 Claims, No Drawings

PREPARATION OF DIALKYL MALONATES

The present invention relates to a process for preparing dialkyl malonates by ozonolysis of diketene and subsequent catalytic hydrogenation and esterification of the reaction products.

The preparation of malonic anhydride and substituted malonic anhydrides by ozonolysis of the enol lactone dimer of ketene, called diketene, has been disclosed. The malonic anhydrides produced thereby can be hydrolyzed with water to the corresponding acid, reacted with alcohols to give the corresponding monoesters or converted with an amine into the monoamide (U.S. Pat. No. 4,360,691 and U.S. Pat. No. 4,251,477). This reaction takes place very easily, as characteristic of the four-membered ring of malonic anhydride. However, it is evident from these citations that much more forcing conditions must be used to convert the monoester or the monoamide into the corresponding diesters, diamides or ester amides, for example treatment of the monoester or monoamide with thionyl chloride, followed by reaction of the resulting ester chlorides or amide chloride compound with further alcohol or amine. Examples 2 in the two U.S. patents agree in stating that only 76% of the expected malonic monoester was isolated when the reaction was carried out in this way. According to Examples 3, only 76% of malonic monoester is obtained with unsubstituted diketene too.

The working up of the reaction mixture is difficult owing to the peroxy compounds which occur. The reaction products have to be isolated by alkaline extraction from the reaction mixture and obtained from this extract by washing with ether several times after acidification. As mentioned above, further reaction steps are necessary to obtain, for example, the diesters.

However, the essential reaction products are the malonic diesters because these are of economic importance and can be used, for example, for synthesizing barbituric acid.

It is an object of the present invention to provide a process with which it is possible to prepare dialkyl malonates in high yield straightforwardly and, where possible, without the occurrence of by-products which cannot be used.

We have found that this object is achieved by a process in which dialkyl malonates and, in addition, dialkyl acetals and alkyl formates are produced, and which comprises a) ozonizing diketene in a $C_1$-$C_6$-alkanol, b) subsequently catalytically hydrogenating the reaction mixture and c) then heating, with the addition of catalytic amounts of acid, to form the dialkyl acetals and dialkyl malonates.

The dialkyl malonates can be prepared in high yields by this reaction sequence, although malonic acid and malonic anhydride are known to be thermally unstable.

The reaction sequence according to the invention can be depicted diagrammatically as follows:

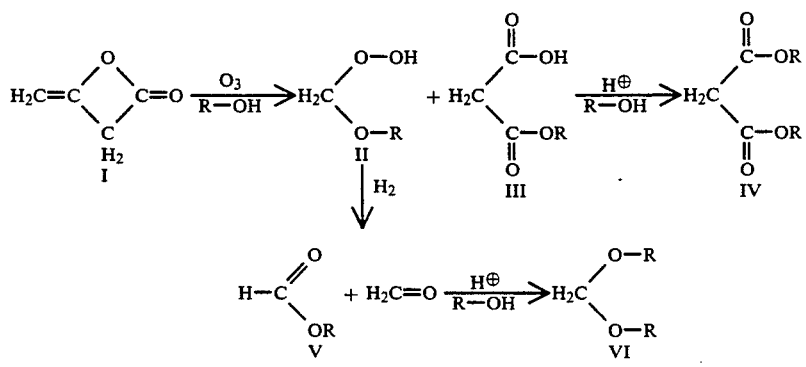

Diketene (I) is ozonized in a $C_1$-$C_6$-alkanol, the initial products being a hydroperoxy hemiacetal (II) and a malonic monoester (III). The subsequent catalytic hydrogenation converts (II) into an alkyl formate (V) and formaldehyde. On addition of catalytic amounts of acid, for example under the conditions of azeotropic esterification, the formaldehyde is converted into the dialkyl acetal (VI), also called dialkylformal, and the monoester (III) is converted into the required dialkyl malonate (IV).

The entire reaction can be carried out as a one-pot reaction. Preferred alcohols are $C_1$-$C_4$-alkanols, especially methanol and ethanol.

The reaction can be carried out either continuously or batchwise.

A particular advantage of the process according to the invention is that the resulting by-products can also be used, and the occurrence of interfering reaction products is substantially avoided. Thus, reaction of the hydroperoxy hemiacetal (II) which occurs as intermediate gives formaldehyde which would slowly escape during conventional working up by distillation and lead to contamination with paraformaldehyde. This is substantially avoided by the way the reaction is carried out according to the invention.

The following comments should be made on the individual reaction steps:

The ozonolysis takes place, for example, in a flask with gas-introducing stirrer, and the ozone is generated together with oxygen in a conventional manner and is passed into the diketene and the alcohol. The reaction mixture is preferably at from $-60°$ C. to $+30°$ C. Reaction is allowed to continue until the diketene has been consumed, which is evident from the blue coloration caused by unreacted ozone. The ozonolysis can also be carried out at room temperature, when, surprisingly, although the reaction of the diketene with ozone takes place more rapidly than the likewise possible reaction with the alcohol, on the other hand the malonic monoester is formed so rapidly that there is negligible formation of decomposition products.

The subsequent hydrogenation is carried out with conventional hydrogenation catalysts such as palladium or platinum on active carbon or Raney nickel, preferably at from $-60°$ C. to $+30°$ C. The hydrogenation is preferably carried out with the $H_2$/Pd/active carbon.

Even if the ozonolysis has been carried out at low temperatures, the hydrogenation reaction mixture can be warmed to room temperature.

The alkyl formate (V) can be removed after the hydrogenation, preferably by distillation before or after reaction step c). The methyl formate which is produced in a preferred embodiment of the process in methanol can be removed by distillation, for example, at this point in the process, i.e. before the esterification. It is a valuable starting material for formic acid, formamide or dimethylformamide, for example.

The subsequent esterification of the malonic monoester (III) with simultaneous formation of the dialkyl acetal (V) is carried out under the conditions conventional for acid-catalyzed esterification. For this, the residue from the hydrogenation, where appropriate after removal of the alkyl formate, is taken up in an inert solvent, e.g. toluene, mixed with a catalytic amount of acid, e.g. p-toluenesulfonic acid, and heated. The water formed in the reaction is removed azeotropically, the dialkyl malonates and dialkyl acetals resulting in reaction step c) are preferably worked up by distillation. It is possible to obtain the dimethyl acetal in the case of R-OH=methanol as fore-run. The dimethyl acetal (methylal) is likewise an interesting product. It either can be used in the catalytic dehydrogenation of methanol for preparing formaldehyde, which makes it possible to achieve higher formaldehyde concentrations, or is used as highly polar solvent very resistant to alkalis.

The combination of the process steps according to the invention provides a process which is straightforward to carry out and gives high yields of dialkyl malonates, and is associated with economic use of the ozonolysis products which are otherwise unwanted.

EXAMPLE 304 g (3.62 mol) of 98% pure diketene and 1.5 l of methanol were introduced into a flask which was equipped with a high-speed gas-introducing stirrer. 200 l of oxygen with an ozone content which meant that 20.5 g of ozone were reacted per hour were passed in at $-40°$ C. After 8¼ hours a blue coloration appeared, which indicated that the diketene was consumed. The peroxide content of the solution, determined by iodometry, was then 97.5% of theory.

Then 5 g of catalyst containing 5% palladium on active carbon were added at $-40°$ C. During the subsequent hydrogenation the temperature rose over the course of one hour from $-40°$ C. to $+10°$ C. The total amount of hydrogen consumed was only 26.2 l, which corresponds to only 33% of the amount necessary to hydrogenate the peroxy acetal.

134 g of methyl formate were then removed by distillation; this corresponds to 92% of the amount expected from the hydrogen consumption.

For the subsequent esterification, 700 ml of toluene and 3 g of p-toluenesulfonic acid were added and the water of reaction was removed azeotropically with a trap. The fore-run comprised 81 g of methylal in the form of an azeotrope with 9.2% methanol distilling at $42°$ C., and this corresponds to 89% of the amount expected from the hydrogen consumption.

After no further water was trapped, the solvents such as toluene and methanol were removed by distillation, and 420 g of dimethyl malonate were isolated as the last fraction under reduced pressure (boiling point $45°-50°$ C. under 0.1 mbar). Gas chromatography showed that this was 97.5% pure. The yield was accordingly 87.5% based on diketene used.

We claim:
1. A process for preparing dialkyl malonates, which comprises
   a) ozonizing diketene in a $C_1-C_6$-alkanol at a temperature of from $-60°$ C. to $+30°$ C.,
   b) subsequently catalytically hydrogenating the reaction mixture within said temperature range of from $-60°$ C. to $+30°$ C., and
   c) then heating the hydrogenated reaction mixture, with the addition of catalytic amounts of acid, to form the dialkyl malonates.

2. The process of claim 1, wherein $C_1-C_4$-alkanols, are employed as alcohols.

3. The process of claim 1, wherein reaction step c) is carried out under the conditions of azeotropic esterification.

4. The process of claim 1, wherein the alkyl formates resulting as by-products in reaction step b) are removed by distillation before or after reaction step c).

5. The process of claim 1, wherein the dialkyl malonates and dialkyl acetals resulting in reaction step c) are worked up by distillation.

6. The process of claim 1, wherein the catalytic hydrogenation is carried out with $H_2$/Pd/active carbon.

7. The process of claim 1, which is carried out as a one-pot process.